United States Patent [19]

Pohndorf

[11] Patent Number: 4,607,644
[45] Date of Patent: Aug. 26, 1986

[54] SELF-SUTURING POROUS EPICARDIAL ELECTRODE ASSEMBLY

[75] Inventor: Peter J. Pohndorf, Miami Shores, Fla.

[73] Assignee: Cordis Corporation, Miami, Fla.

[21] Appl. No.: 718,463

[22] Filed: Apr. 1, 1985

[51] Int. Cl.[4] .......................... A61N 1/04; A61B 5/04
[52] U.S. Cl. .................................. 128/785; 128/419 P; 128/640; 128/802
[58] Field of Search .................... 128/419 P, 639, 642, 128/784–786, 798, 802

[56] References Cited

U.S. PATENT DOCUMENTS

| Re. 30,366 | 8/1980 | Rasor et al. | 128/786 |
|---|---|---|---|
| 3,244,174 | 4/1966 | Wesbey et al. | 128/785 |
| 3,814,104 | 6/1974 | Irnich et al. | 128/785 |
| 3,880,169 | 4/1975 | Starr et al. | 128/419 P |
| 4,144,889 | 3/1979 | Tyers et al. | 128/419 P |
| 4,306,560 | 12/1981 | Harris | 128/419 P |
| 4,424,818 | 1/1984 | Doring et al. | 128/784 |
| 4,501,276 | 2/1985 | Lombardi | 128/642 |

Primary Examiner—William E. Kamm
Assistant Examiner—Mitchell J. Shein
Attorney, Agent, or Firm—Henry W. Collins; Thomas R. Vigil

[57] ABSTRACT

The self-suturing porous electrode assembly includes an electrode with a finely grained porous coating and a wire, both embedded in a silicone rubber body with a contact face of the electrode protruding from a lower surface of the body. The body is generally planar with pairs of holes therethrough for receiving the legs of U-shaped spring anchor members of surgical spring steel. Each pair of legs is connected at the upper ends thereof to a bight and have at their lower ends sharply pointed outwardly, and downwardly sloping curved prongs which are spring biased outwardly. In an upper armed position the prongs are retained in tensioned condition adjacent the lower surface of the body by means of one or two wedges inserted between the upper surface of the body and the bights. Activation is achieved by removal of the wedges which allows the legs to move downwardly in a spread apart, snap action movement so as to drive the prongs downwardly and outwardly into adjacent myocardial tissue.

10 Claims, 9 Drawing Figures

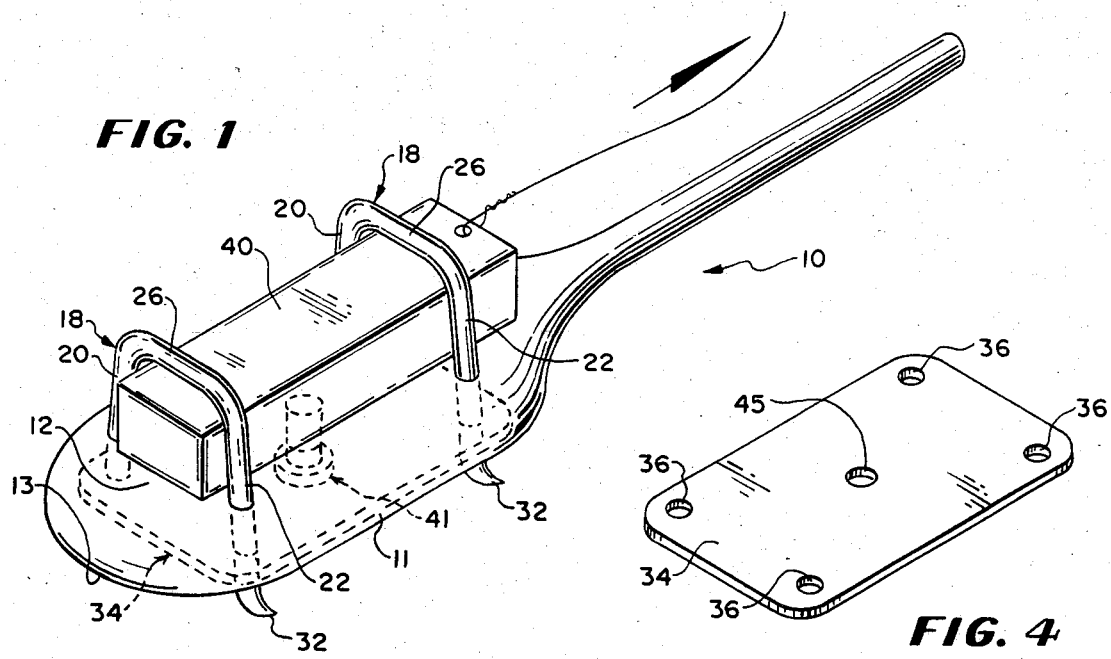
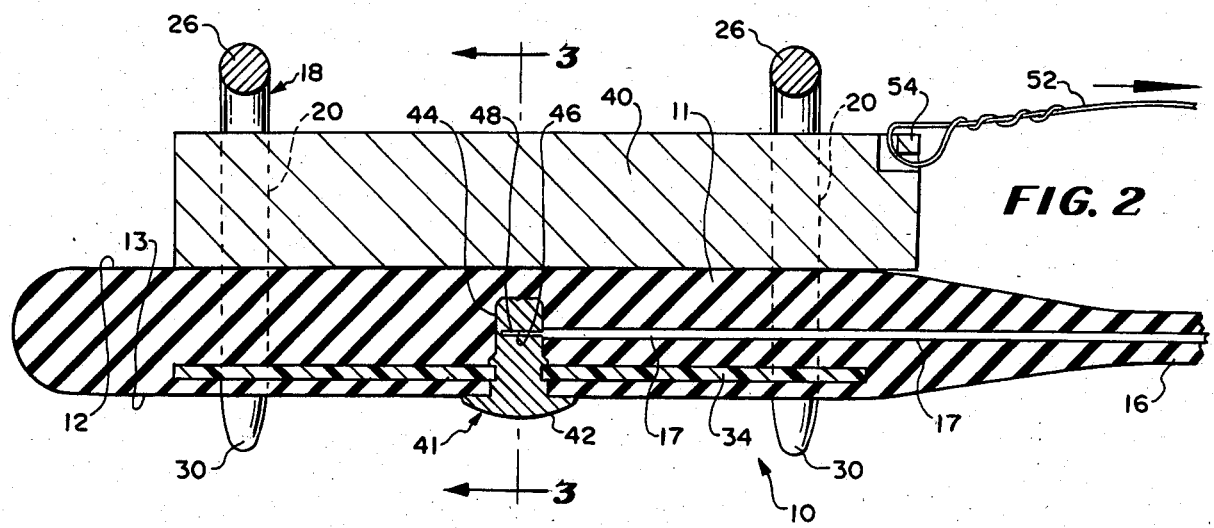
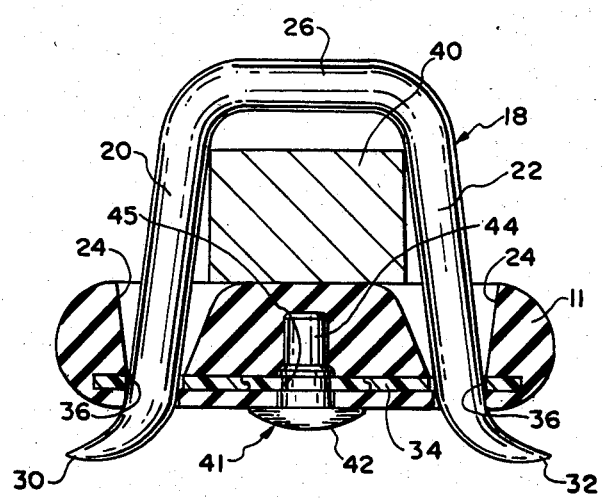

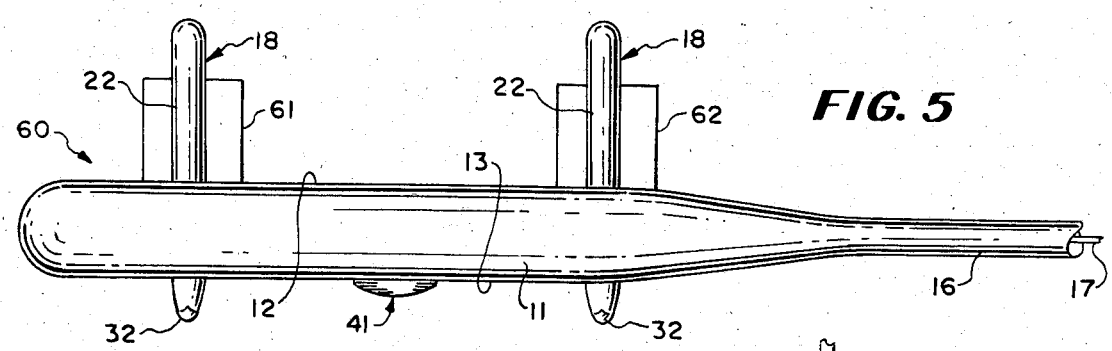
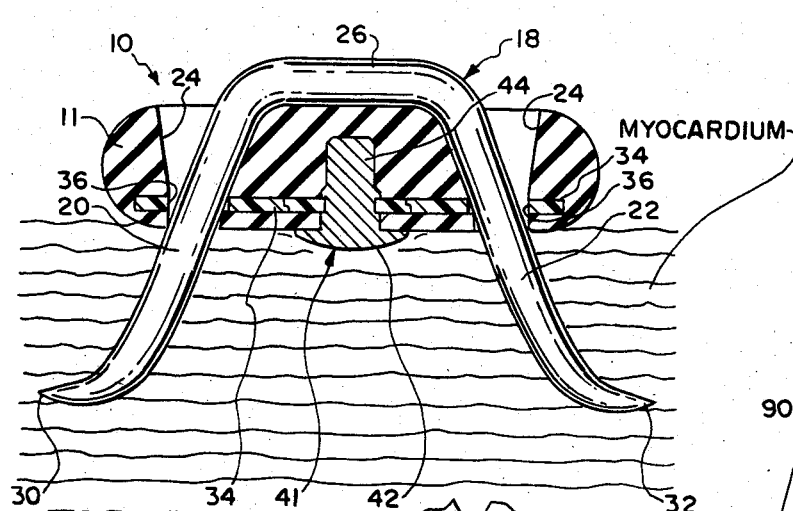
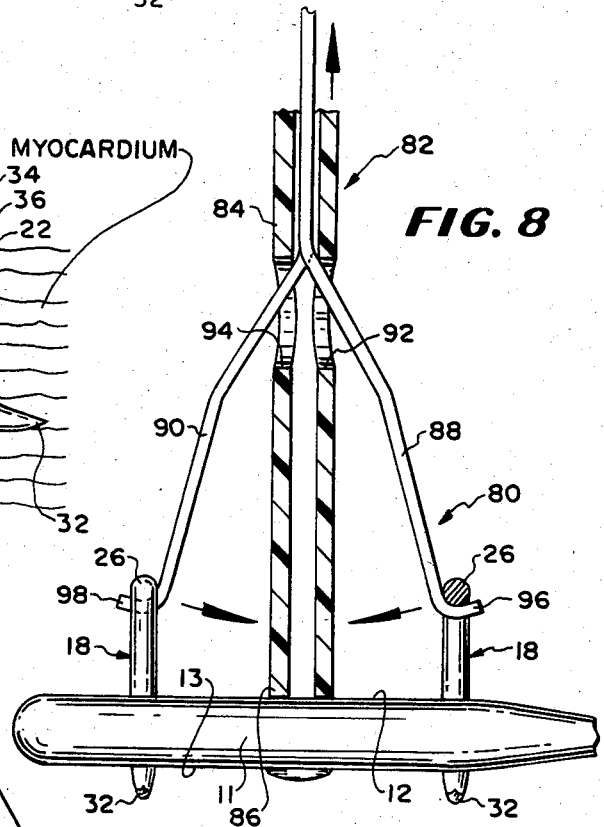
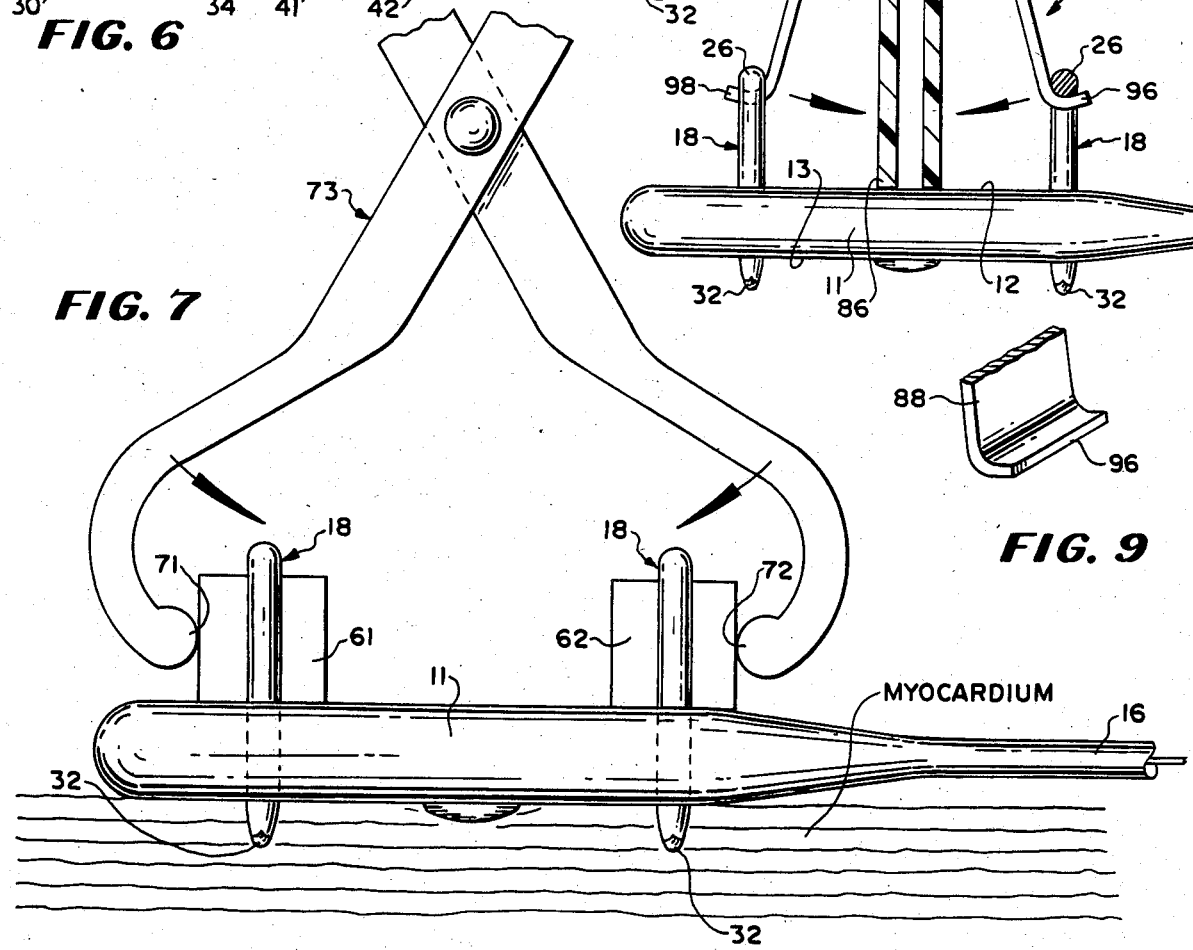
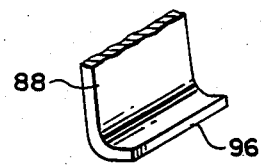

SELF-SUTURING POROUS EPICARDIAL ELECTRODE ASSEMBLY

BACKGROUND OF THE INVENTION

1. Field of the Invention

The present invention relates generally to electrodes for electrical stimulation of heart muscle tissue, and more particularly to an epicardial electrode assembly at the distal end of a pacing lead which is adapted to be connected to a cardiac pacemaker.

2. Description of the Prior Art

A cardiac pacemaker is operable to deliver pacing electrical impulses to an electrode in contact with a heart muscle for ventricular stimulation of the muscle. The electrode is attached to the interior endocardium or the exterior epicardium of the heart muscle, and connected via a flexible pacing lead to the pacemaker which is surgically implanted under the patient's skin.

Typically, an epicardial electrode assembly includes a small electrode body of a flexible silicone rubber. An electrode contact is molded into the rubber body of the electrode assembly and the electrode assembly is sutured to the heart wall using conventional suturing methods.

In order for the surgeon to perform the suturing of the epicardial electrode assembly to the heart muscle in accordance with a conventional method, a thoracotomy is usually required in order to gain access to the heart. The sutures in time cause growth of fibrosis around the electrode assembly which is undesirable since the fibrous tissue reduces the effectiveness of the contact electrode, and in general, the conventional method causes more trauma to the heart than is desirable.

Heretofore various proposals have been made for attaching an electrode assembly to heart muscle in a manner which is faster and with less trauma than prior methods.

For example, the Hess U.S. Pat. No. 4,144,890 discloses a contact device having pointed prongs that are spaced apart from the electrode contact and inserted into the epicardiac wall for securing the device.

The Hess U.S. Pat. No. 4,066,085 discloses a contact device having prong like attaching members with barbs for attaching to the epicardiac wall.

The Rockland U.S. Pat. No. 4,010,758 discloses a bipolar electrode comprising a helix-shaped electrode to be screwed into the heart tissue.

The Rosenbauer U.S. Pat. No. 3,814,104 discloses a unipolar hollow electrode for attachment to a heart having wire hooks that, before attachment, are contained inside the electrode, and during attachment are exposed, extended and penetrate the epicardiac tissue.

The Tachick U.S. Pat. No. 3,472,234 discloses a body organ electrode having a stiff helical member that is screwed into the heart tissue.

The Wesbey U.S. Pat. No. 3,244,174 discloses a body implantable conductor for a pacemaker of bipolar construction with sharply pointed curved electrodes for insertion into the epicardial tissue.

SUMMARY OF THE INVENTION

According to the invention there is provided a self-suturing epicardial electrode assembly comprising a generally flat planar body made of an insulative material and having an upper planar surface, a lower planar surface, and a plurality of holes therethrough between said planar surface, an electrode contact on said lower surface spaced from said holes, spring anchor means being received in said holes and having outwardly pointed prongs which are spring biased under a spring tension away from each other, and releasable means for holding said spring anchor means in an armed position with said prongs adjacent said lower planar surface.

More specifically, the self-suturing epicardial electrode assembly has a generally planar flexible body made of a flexible silicone rubber having an electrode contact on a lower surface for electrical contact with the myocardium. The body contains two U-shaped spring anchor means made of flexible surgical steel. The spring anchor members have transversely oriented legs inserted into an upper surface of the body through holes in the body.

The legs terminate in sharply pointed, outwardly facing, curved prongs. The spring anchor members are, before attachment to the myocardium, held in a so-called armed position with the legs retracted through the body such as by means of one or more removable wedges that are placed between the upper surface of the body and a bight of each spring anchor member, and hold the legs retracted against their outwardly tensioned spring pressure.

The attachment of the electrode contact to the surface of the heart is undertaken by placing the body against the myocardium and then removing the wedge or wedges, preferably by means of a suitably adapted tool. At the moment the wedge(s) are removed, the spring anchor members expand, driven by the spring tension, and drive the curved sharply pointed prongs downwardly and outwardly into myocardial tissue and firmly hold the body with the electrode contact against the myocardial wall to provide good electrical contact of the electrode contact with the heart muscle.

The spring anchor members can be retained in their armed position by means of an especially adapted tool which is removably attached to the body. Such tool can have retaining feet which can be positioned under the bights of the spring anchor members and which may be retracted rapidly thereby activating the spring anchor member.

The electrode contact also can be coated with a porous metallic material to improve the effectiveness of the electrical contact with the heart muscle.

After attachment, as the heart tissue heals, fibrous tissue grows around the prongs where they have penetrated into the tissue. The fibrous tissue, however, is, due to the construction of the electrode, spatially removed from the electrode contact located in the middle of the lower surface of the body, and will, therefore, not interfere with its operation. The electrode is molded completely into the soft silicone rubber forming the body with only the active electrode contact exposed and is connected to a fine gauge flexible electrical wire conductor which is connected to a heart pacer.

BRIEF DESCRIPTION OF THE DRAWINGS

FIG. 1 is a perspective view of a epicardial electrode assembly and shows spring anchor members retained in an armed position by a removable wedge.

FIG. 2 is a longitudinal, vertical, sectional view of the epicardial electrode assembly shown in FIG. 1 and shows an electrode contact and an electric wire conductor embedded in a silicone rubber body.

FIG. 3 is a lateral, vertical, sectional view of the electrode assembly shown in FIG. 1 and is taken along line 3—3 in FIG. 2.

FIG. 4 is a perspective view of a plastic reinforcement plate which is adapted to be embedded in the silicone rubber.

FIG. 5 is a side elevational view of another embodiment of a epicardial electrode assembly constructed according to the teachings of the present invention and shows the use of two smaller wedges for holding two spring anchor members in armed positions thereof.

FIG. 6 is a lateral, vertical, sectional view similar to the view shown in FIG. 3 after the wedge or wedges are removed and shows the spring anchor members attached to a myocardial wall of a heart.

FIG. 7 is a side elevational view, similar to the view shown in FIG. 5, of the myocardial electrode assembly shown in FIG. 5, and shows part of an activating tool positioned to engage the two wedges for activating the spring anchor members.

FIG. 8 is a side elevational view of the electrode assembly shown in FIG. 7 and shows a special tool for holding the spring anchor members.

FIG. 9 is an enlarged, perspective view of the special tool shown in FIG. 8.

DESCRIPTION OF THE PREFERRED EMBODIMENTS

Referring now to FIGS. 1, 2 and 3, a perspective view of an epicardial electrode assembly 10 is shown in FIG. 1. The electrode assembly 10 includes a generally flat, elongate, silicone rubber body 11 having upper and lower parallel, generally planar surfaces 12 and 13, respectively, a distal end 14 and a proximal end 15 which is connected to or integral with a pacing lead 16 having a wire conductor 17 (FIG. 2) therein which is connected to a heart pacer (not shown) surgically implanted at a suitable location in a patient's body.

The body 11 is made of a soft, flexible silicone rubber, and has inserted through its upper surface 12 two U-shaped spring anchor members 18 made of surgical spring steel. Each spring anchor member 18 has two downward projecting legs 20 and 22 which extend through two respective holes 24 (FIG. 3) in the body 11. The four holes 24 are perpendicular to the planar surfaces 12 and 13.

The two legs 20,22 of each spring anchor member 18 are connected by a bight 26. Each spring anchor member 18 is preformed to a generally U-shape in which the legs 20,22 diverge along their length away from the connecting bight 26. The legs 20,22 are inherently biased resiliently toward a laterally diverging or spread-apart configuration and are stressed under a spring tension when held generally parallel in two holes 24 (FIG. 3).

Each downward projecting leg 20 and 22 has a sharply pointed, laterally outwardly projecting, curved prong 30 and 32.

A reinforcing plate 34 is embedded in the electrode body 11. The reinforcing plate 34 is made of a strong substantially rigid plastic material and has holes 36 (FIG. 4) that are in registry with the holes 24 in the body 11 for receiving the legs 20,22 of the spring anchor member 18. The reinforcing plate 34 serves to provide additional strength for the electrode assembly 10, and more particularly to retain the legs 20,22 of each spring anchor member 18 parallel against the spring tension of the legs 20,22 since the soft silicone rubber material of the body 11 may not be strong enough to retain the legs 20,22 parallel.

A removable elongate wedge 40 is positioned between the bight 26 of each spring anchor member 18 and the upper planar surface 12 of the body 11, and serves to retain the spring anchor member 18 in an upper armed position as shown. The prongs 30,32 are positioned adjacent the lower planar surface 13 of the body 11 just beneath the holes 24 against the spring tension of the legs 20,22.

The body 11 has partially embedded therein, an electrode 41 having an exposed electrode contact 42 which faces downward from the planar surface 13 for making electrical contact with the epicardium. The electrode 41 has an upward projecting shank 44 which extends upward through, and is fixed in, a central opening 45 in the reinforcing plate 34 that is completely embedded in the rubber body 11.

As shown in FIG. 3, the shank 44 has a laterally oriented mounting hole 46, which receives a distal end 48 of the wire conductor 17. The wire conductor 17 is embedded in the silicone rubber body 11 and in the pacing lead 16, and is connected to the heart pacer (not shown). The wire conductor 17 conducts heart pacing, electrical pulses from the heart pacer through the electrode contact 42 and to the heart muscle.

The body 11 may be molded integral with the pacing lead 16, thereby forming a unitary assembly without material discontinuities.

The activation of the spring anchor member 18 is performed by a surgeon by first placing the body 11 with the planar underside 13 having the electrode contact 42 against the myocardium and then quickly removing the wedge 40 from its position shown in FIG. 1 by suitable means such as by pulling a string 52 attached to a proximal end 54 of the wedge 40, to completely withdraw the wedge 40 from engagement with the spring anchor member 18. When the wedge 40 is removed, the outwardly biased legs 20 and 22 of each spring anchor member 18 which bear against the laterally outward edges of the holes 36 in the reinforcement plate 34, slide and snap downwardly and laterally outwardly causing the pointed curved prongs 30,32 to penetrate the myocardial wall and embed themselves firmly therein, as shown in FIG. 6. In this way, the body 11 is secured to the myocardial wall so as to press the dome-shaped face of the electrode contact 42 against the myocardial wall.

After implantation, as the myocardiac tissue heals from the stab wounds created by the penetration of the prongs 30,32 fibrous scar tissue grows around the prongs 30,32, and since the prongs 30,32 are projecting away from the electrode contact 42, no scar tissue develops at or in the vicinity of the electrode contact 42 which could create interference with the electrical connection between the electrode contact 42 and the myocardial tissue.

Since the tissue immediately adjacent the electrode contact 42 remains unaffected by scar tissue, the use of an electrode contact 42 with a metallic porous contact coating is especially effective mainly due to the fact that a porous electrode coating enhances the formation of stabilized surface tissue in that area of the myocardial wall that is in direct contact with the face of the electrode contact 42. This layer operates to retain the electrode contact 42 in a stable position relative to the myocardial tissue.

Electrodes having a porous metallic coating are known. For example, U.S. Pat. No. 4,280,514 to MacGregor discloses a porous electrode. A porous electrode typically comprises a finely grained metallic surface which contains a large number of microscopic pores, which as stated above, by contact with the epicardiac tissue stimulates the formation of a tissue layer in the boundary zone, between the heart and the porous contact surface.

FIG. 5 shows an electrode assembly 60 in which the single wedge 40 shown in FIG. 1 is replaced by two small shorter wedges 61 and 62 each disposed under the bights 26 of each of the spring anchor members 18.

FIG. 7 shows the electrode assembly 60 with spring anchor members 18 in the armed position placed against the surface of the heart muscle, at the moment immediately prior to activation. Tips 71 and 72 of a pair of specially adapted forceps 73 are shown positioned to engage ends 74 and 76 respectively of the wedges 61 and 62. In order to activate the spring anchor members 18, a surgeon, operates the forceps 73, to push the wedges 61 and 62 inwardly out of engagement with the spring anchor members 18 causing them to snap open and attach themselves to the myocardial wall.

FIG. 8 shows a myocardial electrode assembly 80 which includes an activating tool 82 instead of a wedge 40 or wedges 61 and 62 for simultaneously holding and manipulating the body 11 and for retaining the spring anchor members 18 in their armed position.

The activating tool 82 comprises a tube 84 having a lower distal end 86 positioned against the upper surface 12 of the body 11.

Two resilient flat wires 88,90 enter the tube 84 from above and exit the tube 84 from two opposed holes 92,94 in the tube 84 above the upper surface 12. Outside the tube 84, the flat wires 88,90 continue downwardly and terminate in two transverse, outwardly facing hook shaped feet 96,98 which hook under the bight 26 of each spring anchor members 18 and retain them in their upper, armed position, as shown.

FIG. 9 shows an enlarged view of the foot 96.

In the armed position, as shown, the resilient flat wires 88,90 exert an outward and upward force on the spring anchor members 18. Then, when the flat wires are pulled upwardly in the tube 84, they are caused to move inwardly toward the tube 84 away from the spring anchor members 18 allowing them to snap into the myocardium.

Activation of the spring anchor members 18 is performed by the surgeon by means of a sharp upward pull of the flat wires 88 and 90 relative to the tube 84. The upward pull draws the resilient flat wires 88 and 90 inward and releases the feet 96,98 from under the bight 26 of the spring anchor members 18, so that the spring tensioned curved prongs 30,32 are driven by their own spring tension downwardly and outwardly into the myocardial wall.

From the foregoing description, it will be apparent that the epicardial electrode assembly 10, 60 or 80 of the present invention has a number of advantages some of which have been described above and others of which are inherent in the invention. Also, modifications can be made to the assemblies 10, 60 and 80 without departing from the teachings of the invention. Accordingly, the scope of the invention is only to be limited as necessitated by the accompanying claims.

I claim:

1. A self-suturing epicardial electrode assembly comprising:
   a generally planar body made of a flexible rubber-like material, said body having upper and lower substantially parallel surfaces and at least two pairs of holes through said body, extending substantially perpendicular to said upper and lower surfaces;
   an electrode embedded in said said body, said electrode having a downward facing electrode contact face which is exposed below said lower surface of said body for engagement with the myocardial wall of a heart;
   an insulated electrode wire conductor embedded at its distal end in said body and conductively attached to said electrode, said wire conductor extending from said body into a pacing lead;
   at least two spring anchor members, each spring anchor member having a pair of downwardly projecting, outwardly tensioned legs mutually attached at their upper ends to a bight, each leg at its lower end terminating in an outwardly and downwardly projecting, sharply pointed, curved prong, each of said pairs of legs being received in one of said pairs of holes, each of said spring anchor members having an upper armed position and a lower activated position, said prongs in said armed position being adjacent said lower surface of said body and in said activated position being capable of penetrating the myocardial wall of a heart and operating to secure said body to said myocardial wall;
   means for retaining said spring anchor members in said armed position; and
   means for removing said means for retaining said spring anchor members in said armed position.

2. The self-suturing electrode assembly according to claim 1 wherein said means for retaining said spring anchor members in said armed position further comprise at least one wedge, said wedge being disposed in the space between the bight of each of said spring anchor members and said upper surface of said body.

3. The self-suturing electrode assembly according to claim 2 wherein said means for retaining said spring anchor members in said armed position comprises at least two small wedges, each small wedge being disposed in one of the spaces between said upper surface of said electrode body and the bight of one of said spring anchor members.

4. The self-suturing electrode assembly according to claim 3 wherein said means for removing said means for retaining said spring anchor members is a specially adapted pair of forceps, said pair of forceps having mutually inwardly facing tips for removal of said small wedges.

5. The self-suturing electrode assembly according to claim 2 including a pull string having one end attached to a proximal end of said wedge.

6. The self-suturing electrode assembly according to claim 1 wherein said means for retaining said spring anchor members in said armed position is a specially adapted tool, said tool comprising a tube, at least two resilient parallel wires in said tube, each wire corresponding to one of said spring anchor members, said tube having a proximal end and a distal end adapted to rest on said upper surface, each wire terminating in a transverse foot at the distal end thereof, said tube having opposed openings above the lower distal end thereof each wire extending from one of said openings in said tube with each foot hooking under a respective bight of one of said spring anchor members, said specially adapted tool operating to release said spring anchor members when said wires are pulled upwardly through said tube toward said proximal end of said tube, thereby to withdraw said feet from said spring anchor members.

7. The self-suturing electrode assembly according to claim 1 further comprising a reinforcement plate, said plate being embedded in said body between, and parallel with, said upper surface and said lower surface, said plate having a plurality of plate holes, said plurality of plate holes being equal in number to said plurality of transversely oriented holes in said body and aligned therewith, said plate holes operating to receive and confine legs of said spring anchor members in said armed position.

8. The self-suturing electrode assembly according to claim 6, wherein said electrode has an upwardly projecting electrode shank and said reinforcement plate has a central hole for receiving said electrode shank.

9. The self-suturing electrode assembly according to claim 1 wherein said contact face of said electrode is a porous electrode contact face.

10. A self-suturing epicardial electrode assembly comprising a generally flat and planar body made of an insulative material and having an upper planar surface, a lower planar surface and a plurality of holes therethrough between said planar surfaces, an electrode having a contact face on said lower surfaces spaced from said holes, spring anchor means being received in said holes, having outwardly pointed prongs which are spring biased under a spring tension away from each other, releasable means for holding said spring anchor means in an armed position with said prongs adjacent said lower surface, and means for releasing said holding means to allow said prongs to move downwardly and outwardly under the force of the spring tension and into myocardial tissue.

* * * * *

UNITED STATES PATENT AND TRADEMARK OFFICE
CERTIFICATE OF CORRECTION

PATENT NO. : 4,607,644

DATED : August 26, 1986

INVENTOR(S) : Peter J. Pohndorf

It is certified that error appears in the above-identified patent and that said Letters Patent is hereby corrected as shown below:

Column 7, line 18, "6" should be --7--.

Signed and Sealed this

Twenty-fourth Day of February, 1987

*Attest:*

DONALD J. QUIGG

*Attesting Officer*    *Commissioner of Patents and Trademarks*